United States Patent [19]

Bessay et al.

[11] Patent Number: 4,500,256
[45] Date of Patent: Feb. 19, 1985

[54] GUIDE BLADE SET FOR DIVERGING JET STREAMS IN A STEAM TURBINE

[75] Inventors: Raymond Bessay, Belfort; Gilbert Riollet, Paris, both of France

[73] Assignee: Alsthom-Atlantique, Paris, France

[21] Appl. No.: 475,562

[22] Filed: Mar. 15, 1983

[30] Foreign Application Priority Data

Mar. 19, 1982 [FR] France ............................... 82 04687

[51] Int. Cl.³ .............................................. F01D 19/02
[52] U.S. Cl. ..................................... 415/191; 415/210
[58] Field of Search ........... 415/181, 185, 191, 213 C, 415/210, 207, 218, 217

[56] References Cited

U.S. PATENT DOCUMENTS

| 1,475,212 | 11/1923 | Warren et al. | |
| 2,650,060 | 8/1953 | Stalker | 415/191 X |
| 3,056,583 | 10/1962 | Varadi et al. | 415/218 |
| 3,347,520 | 10/1967 | Owczarek | 415/218 X |
| 3,625,630 | 12/1971 | Soo | 415/210 UX |
| 4,165,949 | 8/1979 | Riollet | 415/213 C X |

FOREIGN PATENT DOCUMENTS 235180 8/1925 United Kingdom .

Primary Examiner—Robert E. Garrett
Assistant Examiner—Joseph M. Pitko
Attorney, Agent, or Firm—Sughrue, Mion, Zinn, Macpeak, and Seas

[57] ABSTRACT

A guide blade set for diverging jet streams in a steam turbine which has blades (2) disposed between a floor plate (3) and a ceiling plate (4) and whose concave and convex surfaces are constituted by substantially rectilinear generator lines (l, m, n), wherein said generator lines (l, m, n) of the blades (2) form an angle of about $90° + \theta/2$ with the ceiling plate (4) and with the floor plate (3), where $\theta$ is the angle of divergence of the jet stream.

1 Claim, 7 Drawing Figures

GUIDE BLADE SET FOR DIVERGING JET STREAMS IN A STEAM TURBINE

The present invention relates to a guide blade set for diverging streams in a steam turbine which has blades disposed between a floor plate and a ceiling plate in which the blades have convex and concave surfaces constituted by generator lines which are substantially rectilinear.

BACKGROUND OF THE INVENTION

In known guide vane sets, the generator lines which constitute the convex and concave surfaces of the blades are orthogonal to the floor plate and form an angle of nearly $90° + \theta$ with the ceiling plate, where $\theta$ is the angle of divergence of the stream.

In such blade sets, the wider the angle $\theta$ the higher the secondary losses near the top of the stream.

SUMMARY OF THE INVENTION

To reduce these losses, in the present invention, the guide blade sets form an angle of about $90° + \theta/2$ with the floor plate and with the ceiling plate.

Obviously, said configuration causes an extra loss at the floor plate relative to the conventional configuration, but substantially reduces the loss at the ceiling plate in such a way that the sum of the losses at the ceiling plate and at the floor plate is less than that of conventional configurations.

BRIEF DESCRIPTION OF THE DRAWINGS

The present invention will be better understood from the following description and from the accompanying drawings, in which.

MORE DETAILED DESCRIPTION

Figure 1:
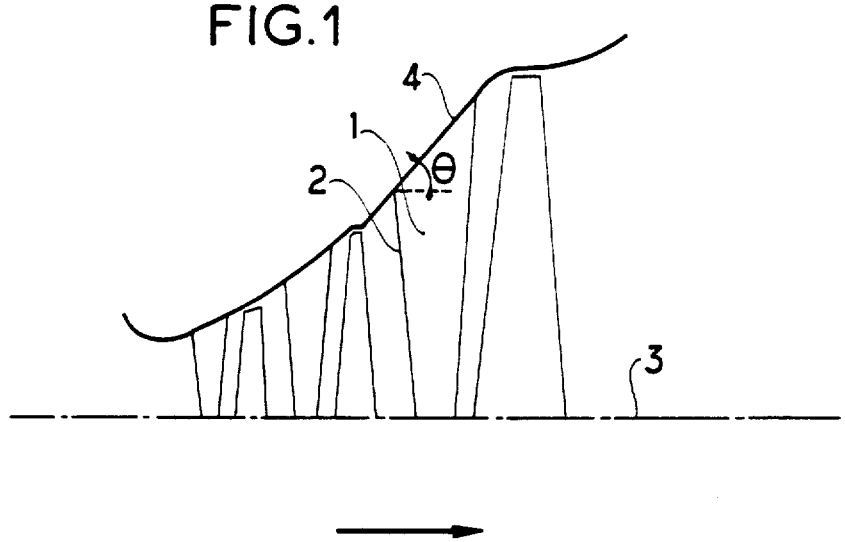
FIG. 1 is an axial cross-section through a diverging flow steam turbine with diverging streams.

FIG. 1 illustrates a steam turbine whose streams diverge in the flow direction.

Said turbine has a succession of stationary and moving blade sets.

A guide blade set 1 of a last stage has blades 2 disposed between a cylindrical floor plate 3 and a conical ceiling plate 4 which forms an angle $\theta$ with the axis OO' of the turbine.

Said angle $\theta$ is particularly wide for the last stage of the low-pressure part of the turbine. Also, when it is required to use moving end blades which are high, said angle is even wider.

In known turbines, the angle $\theta$ at the guide blade set of the last stage usually lies between 25° and 70°.

Figure 2:
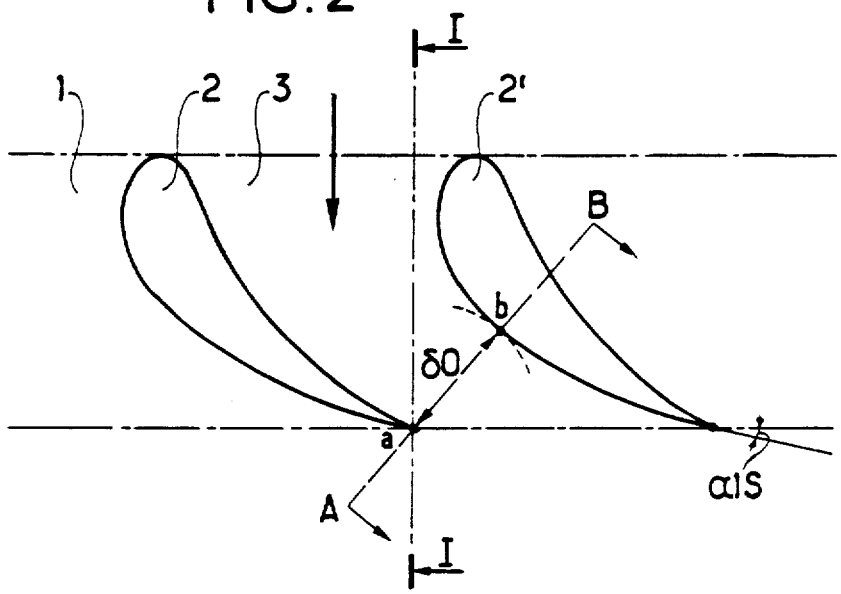
FIG. 2 is a plan view seen from above of the guide blade set.

FIG. 2 is a plan of the guide blade set 1 seen from above, showing two consecutive blades 2 and 2'.

The flow passage 3 is delimited by the concave surface of the blade 2, the convex surface of the blade 2', the ceiling plate and the floor plate.

The minimum distance $\delta 0$ between the two neighbouring blades 2, 2' goes from the end a of the trailing edge of the blade 2 to a point b on the convex surface of the blade 2'. A circle whose centre is said end a and whose radius is $\delta 0$ is tangential at said point b to the convex surface of the blade 2'.

The minimum flow passage cross-section between the two consecutive blades 2 and 2' is defined by the entire height of said two blades and the top and bottom segments a-b.

Figure 3:
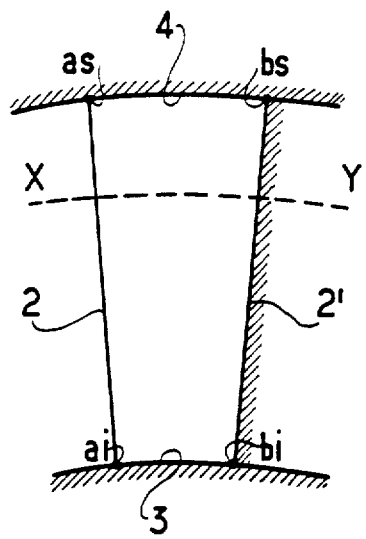
FIG. 3 is a cross-section along line A-B of FIG. 2 for a stream passage which is cylindrical.

When the angle $\theta$ is negligible, said minimum flow passage cross-section is substantially in the shape of a sector of an annulus ai-bi-bs-as (ai and bi being on the floor plate, and as and bs being on the ceiling plate) comprised between the floor plate 3, the ceiling plate 4, the trailing edge of the blade 2 and the convex surface of the blade 2' (see FIG. 3).

Any cylindrical cut XY around the axis of the turbine in the case of FIG. 3 meets all these blades whatever the point at which said cut is made up the height of the blades.

Figure 4:
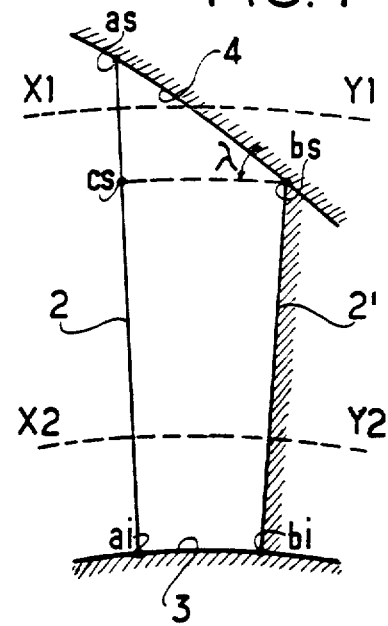
FIG. 4 is the same cross-section as FIG. 3 for a stream passage which is divergent.

When the angle $\theta$ is wide, the flow passage minimum cross-section is in the form of a quadrilateral ai-bi-bs-as (neglecting the curvature of ai-bi on the floor plate 3 and of as-bs on the ceiling plate 4) which differs mainly from the cross-section illustrated in FIG. 3 by the triangle as-bs-cs, where bs-cs is traced parallel to ai-bi (see FIG. 4).

The smaller the exit angle $\alpha$ IS formed between the outlet of the stream and the rear of the blade set, the closer the angle $\lambda$ = as-bs-cs in the triangle as-bs-cs is to the angle $\theta$.

Indeed, the smaller $\alpha$ IS, the more the cross-section passing through a and b resembles the cross-section I—I.

Any cylindrical cross-section XY (e.g. X2-Y2) which passes through the turbine shaft at a level lower than bs-cs meets the blades.

Figure 5:
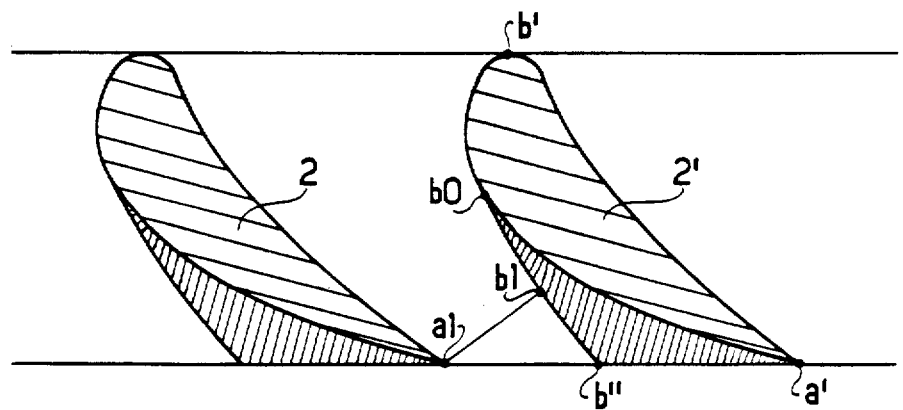
FIG. 5 is a cross-section X-Y at the level X1-Y1 of FIG. 4.

In contrast, any cross-section XY such as X1 Y1 made on the portion of the blade between as and cs passes through the blade 2 but no longer passes through the blade 2' (see said cross-section in FIG. 5).

The flow passage cross-section is determined firstly by the concave surface of the blade 2 and secondly by the convex surface of the blade 2' in a first part b'-bo; then by the ceiling plate from bo to b''.

In particular, because of the extra thickness b0-b''-a' where a' is the intersection of the trailing edge of the blade 2' by the cylinder X1 Y1 (where X1 Y1 lies between as and cs), great losses occur when the steam which passes through the triangle as bs cs expands.

Figure 6:
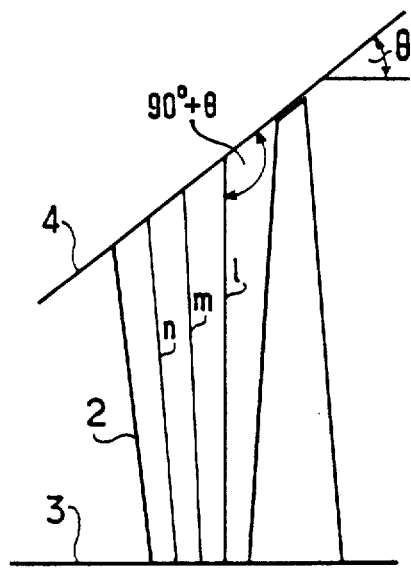
FIG. 6 shows a conventional stream.

FIG. 6 illustrates a conventional blade. The substantially rectangular generator lines (l, m, n) forming the convex and concave surfaces are orthogonal to the floor plate and form an angle of $\theta + 90°$ with the ceiling plate 4.

Figure 7:
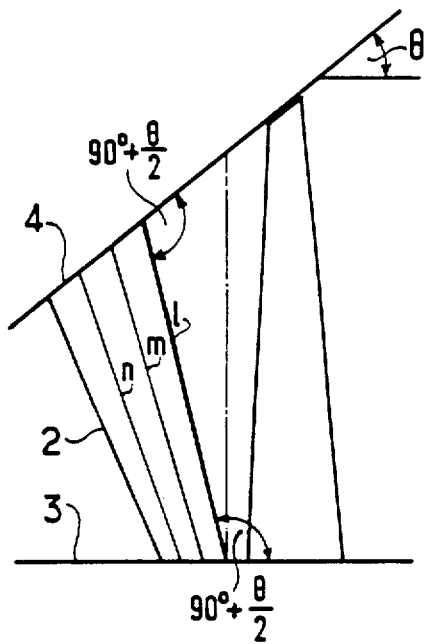
FIG. 7 shows a stream in accordance with the invention.

In FIG. 7, the guide blade set is inclined so that the generator lines (l, m, n) form an angle $\theta/2 + 90°$ with the ceiling plate 4 and also with the floor plate 3.

We claim:

1. A guide blade set for diverging streams in a steam turbine which has blades disposed between a floor plate and a ceiling plate, said floor plate extending generally parallel to the axis of the turbine, said ceiling plate being conical and forming an angle $\theta$ with the axis of the turbine, the improvement wherein the blades are curved such that concave and convex surfaces of said blades at one end thereof defined by substantially linear generator lines form an angle of substantially $90° + \theta/2$ with the floor plate, and an angle of substantially $90° + \theta/2$ with said ceiling plate, where $\theta$ is the angle of divergence of the jet stream.

* * * * *